(12) United States Patent
Rolshausen

(10) Patent No.: US 10,159,256 B2
(45) Date of Patent: Dec. 25, 2018

(54) ORGANIC PRUNING WOUND COMPOSITION

(71) Applicant: The Regents of the University of California, Oakland, CA (US)

(72) Inventor: Philippe Rolshausen, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/313,709

(22) PCT Filed: May 26, 2015

(86) PCT No.: PCT/US2015/032484
§ 371 (c)(1),
(2) Date: Nov. 23, 2016

(87) PCT Pub. No.: WO2015/183833
PCT Pub. Date: Dec. 3, 2015

(65) Prior Publication Data
US 2017/0202225 A1    Jul. 20, 2017

Related U.S. Application Data

(60) Provisional application No. 62/002,985, filed on May 26, 2014.

(51) Int. Cl.
| | |
|---|---|
| A01N 61/00 | (2006.01) |
| A01N 61/02 | (2006.01) |
| A01N 59/16 | (2006.01) |
| A01N 59/14 | (2006.01) |
| A01N 47/34 | (2006.01) |
| A01N 3/04 | (2006.01) |

(52) U.S. Cl.
CPC ............. *A01N 61/00* (2013.01); *A01N 3/04* (2013.01); *A01N 47/34* (2013.01); *A01N 59/14* (2013.01); *A01N 59/16* (2013.01); *A01N 61/02* (2013.01)

(58) Field of Classification Search
None
See application file for complete search history.

(56) References Cited

U.S. PATENT DOCUMENTS

| | | | |
|---|---|---|---|
| 2,382,326 A | 8/1945 | Mecca et al. | |
| 4,612,193 A * | 9/1986 | Gordon | A61K 9/0048 424/644 |
| 4,897,427 A | 1/1990 | Barnovon et al. | |
| 5,478,598 A * | 12/1995 | Shiozawa | B27K 3/15 106/15.05 |
| 5,817,369 A * | 10/1998 | Conradie | B27K 3/52 106/18.13 |
| 5,993,891 A * | 11/1999 | Danielson | A01G 17/18 106/15.05 |
| 6,183,766 B1 | 2/2001 | Sine et al. | |
| 2003/0049281 A1 * | 3/2003 | Espinoza | A61K 8/14 424/400 |
| 2004/0013744 A1 | 1/2004 | Goulbourne | |
| 2005/0202097 A1 * | 9/2005 | Maskin | A61K 35/60 424/524 |

FOREIGN PATENT DOCUMENTS

| | | |
|---|---|---|
| DE | 39 09 962 A | 9/1990 |
| DE | 3909962 A1 | 9/1990 |
| EP | 1787637 A2 * | 5/2007 ........... A61K 9/0017 |
| EP | 1787637 A2 | 5/2007 |
| FR | 1 401 330 A | 6/1965 |
| FR | 1401330 A | 6/1965 |
| GB | 2 271 579 A | 4/1994 |
| GB | 2271579 A | 4/1994 |
| HU | 203 936 B | 11/1991 |
| HU | 203936 B | 11/1991 |
| JP | 2002 000093 A | 1/2002 |
| JP | 2002000093 A | 1/2002 |
| WO | 01/30363 A1 | 5/2001 |
| WO | 03/020037 A1 | 3/2003 |
| WO | 2013/060147 A1 | 5/2013 |

OTHER PUBLICATIONS

Slack Wax—Products (Year: 2017).*
Zinc Sulfate—The Merck Index Online, 2017 (Year: 2017).*
Zinc chloride—Merck Index Online, 2017 (Year: 2017).*
Boric Acid—Merck Index Online, 2017 (Year: 2017).*
Zinc Sulfate—The Merck Index, 2001 (Year: 2001).*
Thomas, Shane, International Search Report and Written Opinion, PCT/US2015/032484, United States Patent & Trademark Office, dated Jul. 16, 2015.
Nickitas-Etienne, Athina, International Preliminary Report on Patentability and Written Opinion, PCT/US2015/032484, The International Bureau of WIPO, dated Dec. 8, 2016.
Marie, Gerald, Extended European Search Report, European Patent Office, Application No. EP15800125.5, dated Oct. 25, 2017.
Fitzgibbon, Colin, First Office Action, Patent Application No. 2015267245, Australian Patent Office, dated Apr. 11, 2018.
Office Action, Chile Patent Office, 2016-003037, dated Jul. 17, 2018.

* cited by examiner

*Primary Examiner* — Sue X Liu
*Assistant Examiner* — Thor Nielsen
(74) *Attorney, Agent, or Firm* — Gavrilovich, Dodd & Lindsey LLP

(57) ABSTRACT

The disclosure describes a composition for use in treating wounds in trees, plants and vines. In addition, the disclosure provides a method of making the compositions and their use in treating fungal infections of pruning wounds.

7 Claims, No Drawings

ORGANIC PRUNING WOUND COMPOSITION

CROSS REFERENCE TO RELATED APPLICATIONS

This application is a U.S. National Stage Application claiming priority to International Application No. PCT/US2015/032484 filed on May 26, 2015, which application claims priority from U.S. Provisional Application Ser. No. 62/002,985, filed May 26, 2014, the disclosure of which are incorporated herein by reference.

FIELD OF THE INVENTION

The invention relates generally to methods and compositions useful for treating plant diseases, in particular infections by pathogens.

BACKGROUND

California's grape industry needs to maintain a high level of production and quality in order to keep its dominant position nationwide and in the world marketplace. Trunk diseases threaten the long-term longevity, productivity and profitability in all grape production systems.

SUMMARY

The disclosure provides a composition useful as an organic sealant comprising a wax and a softening agent in a ratio of 1:10 to 1:2, but preferably 1:5. In one embodiment, the composition comprises a wax selected from the group consisting of polyethylene wax, camuba wax, paraffin wax, polypropylene wax, oxidized polyethylene wax, montan wax, microcrystalline wax, Fischer-Tropsch wax, amide wax, ethylene-acrylic-acid wax, polyolefin wax, ethylene bis stearamide wax, bees wax, lanolin wax, candelilla wax, carnauba wax, esparto grass wax, cork wax, guaruma wax, rice germ oil wax, sugarcane wax, berry wax, ouricury wax, jojoba wax, shea butter, shellac wax, spermaceti, uropygial grease, ceresin, ozocerite (earth wax), sunflower wax, lemon wax, grape fruit wax, laurel wax, vegetable wax and any combination thereof; a softening agent selected from the group consisting of mineral oil, corn oil, casteroil, palm oil, palm kernel oil, soybean oil, cottonseed oil, tall oil, lard oil, oleic oil, rape oil, linseed oil, olive oil, peanut oil, fish oil, soybean oil, sesame oil, hemp seed oil, perilla oil, styrax oil, oiticica oil, kayo oil, walnut oil, cashew oil, poppy seed oil, safflower oil, watermelon seed oil, sunflower oil, rice bran oil, pumpkin seed oil, tsubaki oil, crystalis oil, kaoliang oil, ergot oil, bone oil, shark oil, sardine oil, pike oil, herring oil, saurel oil, cod oil, cuttlefish oil, trout oil, mullet oil, tuna oil, menuke oil, menhadden oil, eel oil, whale oil, liver oil, chinawood oil, plant oil, vegetable oil, animal oil and any combination thereof. The disclosure also provide use of the composition for treating pruning wounds on plants, vines or trees.

The disclosure provides a composition comprising a wax selected from the group consisting of polyethylene wax, camuba wax, paraffin wax, polypropylene wax, oxidized polyethylene wax, montan wax, microcrystalline wax, Fischer-Tropsch wax, amide wax, ethylene-acrylic-acid wax, polyolefin wax, ethylene bis stearamide wax, bees wax, lanolin wax, candelilla wax, carnauba wax, esparto grass wax, cork wax, guaruma wax, rice germ oil wax, sugarcane wax, berry wax, ouricury wax, jojoba wax, shea butter, shellac wax, spermaceti, uropygial grease, ceresin, ozocerite (earth wax), sunflower wax, lemon wax, grape fruit wax, laurel wax, vegetable wax and any combination thereof; a softening agent selected from the group consisting of mineral oil, corn oil, casteroil, palm oil, palm kernel oil, soybean oil, cottonseed oil, tall oil, lard oil, oleic oil, rape oil, linseed oil, olive oil, peanut oil, fish oil, soybean oil, sesame oil, hemp seed oil, perilla oil, styrax oil, oiticica oil, kayo oil, walnut oil, cashew oil, poppy seed oil, safflower oil, watermelon seed oil, sunflower oil, rice bran oil, pumpkin seed oil, tsubaki oil, crystalis oil, kaoliang oil, ergot oil, bone oil, shark oil, sardine oil, pike oil, herring oil, saurel oil, cod oil, cuttlefish oil, trout oil, mullet oil, tuna oil, menuke oil, menhadden oil, eel oil, whale oil, liver oil, chinawood oil, plant oil, vegetable oil, animal oil and any combination thereof; a zinc salt selected from the group consisting of zinc sulfate, zinc acetate, zinc gluconate, zinc chloride, zinc oxide, zinc lactate and any combination thereof; and a boric acid, boronic acid or ester.

The disclosure provides a composition comprising a wax selected from the group consisting of polyethylene wax, camuba wax, paraffin wax, polypropylene wax, oxidized polyethylene wax, montan wax, microcrystalline wax, Fischer-Tropsch wax, amide wax, ethylene-acrylic-acid wax, polyolefin wax, ethylene bis stearamide wax, bees wax, lanolin wax, candelilla wax, carnauba wax, esparto grass wax, cork wax, guaruma wax, rice germ oil wax, sugarcane wax, berry wax, ouricury wax, jojoba wax, shea butter, shellac wax, spermaceti, uropygial grease, ceresin, ozocerite (earth wax), sunflower wax, lemon wax, grape fruit wax, laurel wax and vegetable wax; and a zinc salt and a boric acid, boronic acid or ester. In one embodiment, the wax is bees wax. In another embodiment, the composition further comprises a softening agent that softens the wax. In a further embodiment, the softening agent comprise an oil selected from the group consisting of mineral oil, corn oil, casteroil, palm oil, palm kernel oil, soybean oil, cottonseed oil, tall oil, lard oil, oleic oil, rape oil, linseed oil, olive oil, peanut oil, fish oil, soybean oil, sesame oil, hemp seed oil, perilla oil, styrax oil, oiticica oil, kayo oil, walnut oil, cashew oil, poppy seed oil, safflower oil, watermelon seed oil, sunflower oil, rice bran oil, pumpkin seed oil, tsubaki oil, crystalis oil, kaoliang oil, ergot oil, bone oil, shark oil, sardine oil, pike oil, herring oil, saurel oil, cod oil, cuttlefish oil, trout oil, mullet oil, tuna oil, menuke oil, menhadden oil, eel oil, whale oil, liver oil, chinawood oil, plant oil, vegetable oil and animal oil. In still a further embodiment, the softening agent is mineral oil. In another embodiment, the zinc salt is selected from the group consisting of zinc sulfate, zinc acetate, zinc gluconate, zinc chloride, zinc oxide, and zinc lactate. In a further embodiment, the zinc salt is zinc sulfate. In another embodiment, the composition comprises boric acid, boronic acid. In another embodiment, the zinc salt and boric acid, boronic acid or ester are at a ratio of 1:100 to 100:1. In still a further embodiment, the zinc salt and boric acid, boronic acid or ester are at equal ratios. In still another or further embodiment, the concentration of zinc salt and boric acid, boronic acid or ester are 2.5% of the composition. In another embodiment, the composition is formulated to be sprayed or painted on a wound on a plant, vine or tree. In yet another embodiment, the ratio of the wax and softening agent is about 1:5. In still another embodiment, the wax is beeswax, the zinc salt is zinc sulfate, and the boric acid, boronic acid or ester is a boric acid, boronic acid. In a further embodiment, the composition further comprises mineral oil. In still a further embodiment, the composition comprises a 1:5 ratio of beeswax to mineral oil and the zinc sulfate and boric acid are 2.5% of the composition.

The disclosure also provides a method of making a composition of the disclosure comprising mixing beeswax and mineral oil in a ratio to soften the beeswax; and adding zinc sulfate and boric acid. In one embodiment, the ratio of beeswax and mineral oil is about a 1:5 ratio. In a further embodiment, the boric acid and/or zinc sulfate are added to a final concentration of 2.5%. In another or further embodiment, the method comprises mixing beeswax and mineral oil in a 1:5 ratio to soften the beeswax; melting the beeswax and mineral oil together to a homogenous mixture; allowing the mixture to cool; and adding zinc sulfate and boric acid to a concentration of 2.5%.

The disclosure also provides a composition made by the foregoing method(s).

The disclosure also provides a method of treating plant, vine or tree wound comprising contacting the wound with a composition as described above. In one embodiment, the wound is a pruning wound. In another embodiment, the wound is contacted by painting or spraying the composition of the wound. In still another embodiment, the vine is a grape vine.

The disclosure provides a composition comprising beeswax, zinc and boron. In one embodiment, the composition further comprises a softening agent that softens the beeswax. In another embodiment, the softening agent is mineral oil. In yet another embodiment, the zinc is zinc sulfate. In still another embodiment, the boron is boric acid. In a more specific embodiment, the boric acid is a 2.5% concentration. In yet another embodiment of any of the foregoing, the composition is formulated to be sprayed or painted on a pruning wound.

The disclosure also provides a method of making a composition described above comprising: mixing beeswax and mineral oil in a ratio to soften the beeswax; and adding zinc sulfate and boric acid. In one embodiment, the ratio of beeswax and mineral oil is about a 1:5 ratio. In another embodiment, the boric acid and/or zinc sulfate are added to a final concentration of 2.5%. In still another embodiment the method comprises: mixing beeswax and mineral oil in a 1:5 ratio to soften the beeswax; melting the beeswax and mineral oil together to a homogenous mixture; allowing the mixture to cool; and adding zinc sulfate and boric acid to a concentration of 2.5%. The disclosure also provides a composition made by this method.

The disclosure also provides a method of treating pruning wounds comprising contacting the wound with a composition of the disclosure.

DETAILED DESCRIPTION

As used herein and in the appended claims, the singular forms "a," "and," and "the" include plural referents unless the context clearly dictates otherwise. Thus, for example, reference to "a plant" includes a plurality of such plants and reference to "the pathogen" includes reference to one or more pathogens known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Any publications discussed herein are provided solely for their disclosure prior to the filing date of the present application. Nothing herein is to be construed as an admission that the inventors are not entitled to antedate such disclosure by virtue of prior disclosure.

Crop infestations can cause severe damage to crop production and can cause severe economic harm to farmers and consumers. Plant hosts can include miscellaneous ornamentals, grape, oleander, oak, almond, peach, pear, citrus, coffee, maple, mulberry, elm, sycamore, and alfalfa.

The importance of trunk diseases to stakeholders was highlighted by a recent annual survey conducted by the American Vineyard Foundation where trunk diseases was ranked $9^{th}$ on a list of 42 research priorities. In California, the cost to the wine industry from trunk disease was estimated in 1999 at 260 million dollars per year, 16% of the gross producer revenue. However, this figure did not take into account the losses in table or raisin grape production. Table grape growers can experience losses due to blemished fruits, which are not marketable.

The causal agents of trunk disease are a set of taxonomically unrelated Ascomycete fungi among which *Eutypa lata*, *Botryosphaeiaceae* species, *Phaeoacremonimum* species and *Phaemoniella chlamydospora* are the most prevalent. These fungi infect grapevines through pruning wounds. Because pruning is necessary to achieve economically viable yields and quality coupled with the fact that no methods exist to eradicate these fungi, trunk disease is a persistent problem. Fungal spores become airborne with rain, land on the wounded surface, colonize the wood and form cankers. Cultural practices and sanitation of vineyards can decrease the incidence and the severity of these diseases but fungicide applications applied shortly after pruning is the most effective management strategy.

TOPSIN® M (United Phosphorous, Inc.) and RALLY® (Dow AgroSciences) are the two fungicides currently registered in California for trunk disease. TOPSIN M is known to be effective against trunk disease while data for RALLY are currently being evaluated.

Initial data indicate that one post-pruning spray application of 1% TOPSIN M provided good disease control when low to no rainfall occurred after treatment, indicating that this could be an economically sound practice to implement in more arid regions. The application of the commercial product B-LOCK (Nutrient Technologies, Inc.) and DOC FARWELL's GRAFTING SEAL (Farwell Products, Inc.) and 5% boric acid (both products have the same percent active ingredient; boron) also provide good protection against Eutypa dieback and Esca. However, these products are not registered as organic products, leaving organic growers with no alternatives for controlling trunk diseases. The data also indicate that of all the micro- and macronutrients tested, boron (B) and zinc (Zn) were the most effective against *E. lata, Pa. chlamydospora, Pm. Alephilum, P. viticola* and *D. seriata*.

SERENADE MAX (Agraquest), PLANSHIELD (Bioworks, Inc.) and ACTINOVATE AG (Natural Industries, Inc.) are an alternative to conventional fungicides. These products have shown some potential for controlling trunk disease in in vitro tests. However, this potential has not always been demonstrated under field conditions. In addition, the results have also shows that in trials in Sonoma and Santa Clara, Calif., treated wounds had higher infection rates than the non-treated controls suggesting that the treatments themselves may have limited wound colonization with the native microflora that also plays a role in protecting the pruning wound through biological competition. Indeed, apricot tree wounds spayed with fungicides had higher infection rates than control treatments and suggested that this practice may have an impact on the beneficial microflora capable of rapidly colonizing pruning wounds thereby leaving the pruning would vulnerable to pathogen attack.

The disclosure provides an organic zinc- and/or boron-based paste formulation. The disclosure describes the development and implementation of integrated strategies to manage trunk disease that is applicable to any plant that suffers trunk disease (e.g., can be applicable to grape production (including grapes for wine, table and raisins)). The disclosure provides growers with alternative treatments to convention fungicides and, in turn, offer organic growers tools to manage these diseases. The disclosure demonstrates the effects of zinc and/or boron wound composition as fertilizer sprays and as organic paste and their efficacy in comparison to TOPSIN M and RALLY. The disclosure also analyzes the effect of conventional fungicides, fertilizers and bio-pesticide treatments on the dynamics of the native microbial population found on pruning wound surfaces.

The disclosure provides an organic composition comprising a wax that can be used to treat pruning wounds and reduce and/or treat trunk disease. In one embodiment, the organic composition comprises zinc and a wax selected from the group consisting of polyethylene wax, camuba wax, paraffin wax, polypropylene wax, oxidized polyethylene wax, montan wax, microcrystalline wax, Fischer-Tropsch wax, amide wax, ethylene-acrylic-acid wax, polyolefin wax, ethylene bis stearamide wax, bees wax, lanolin wax, candelilla wax, carnauba wax, esparto grass wax, cork wax, guaruma wax, rice germ oil wax, sugarcane wax, berry wax, ouricury wax, jojoba wax, shea butter, shellac wax, spermaceti, uropygial grease, ceresin, ozocerite (earth wax), sunflower wax, lemon wax, grape fruit wax, laurel wax and vegetable wax. In one embodiment, the organic composition comprises boron and a wax selected from the group consisting of polyethylene wax, camuba wax, paraffin wax, polypropylene wax, oxidized polyethylene wax, montan wax, microcrystalline wax, Fischer-Tropsch wax, amide wax, ethylene-acrylic-acid wax, polyolefin wax, ethylene bis stearamide wax, bees wax, lanolin wax, candelilla wax, carnauba wax, esparto grass wax, cork wax, guaruma wax, rice germ oil wax, sugarcane wax, berry wax, ouricury wax, jojoba wax, shea butter, shellac wax, spermaceti, uropygial grease, ceresin, ozocerite (earth wax), sunflower wax, lemon wax, grape fruit wax, laurel wax and vegetable wax. In another embodiment, the organic composition comprises boron and zinc and a wax selected from the group consisting of polyethylene wax, camuba wax, paraffin wax, polypropylene wax, oxidized polyethylene wax, montan wax, microcrystalline wax, Fischer-Tropsch wax, amide wax, ethylene-acrylic-acid wax, polyolefin wax, ethylene bis stearamide wax, bees wax, lanolin wax, candelilla wax, carnauba wax, esparto grass wax, cork wax, guaruma wax, rice germ oil wax, sugarcane wax, berry wax, ouricury wax, jojoba wax, shea butter, shellac wax, spermaceti, uropygial grease, ceresin, ozocerite (earth wax), sunflower wax, lemon wax, grape fruit wax, laurel wax and vegetable wax. In another embodiment, the composition comprises bees wax and zinc. In another embodiment, the composition comprises bees wax and boron. In another embodiment, the composition comprises bees wax, zinc and boron. The composition comprising boron, zinc and beeswax is sometimes referred to herein as "BZwax". The zinc can be in the form of a zinc salt such as, but not limited to, zinc sulfate, zinc acetate, zinc gluconate, zinc chloride, zinc oxide, and zinc lactate.

The composition is useful for treating pruning wounds in plants, trees and vines to control diseases caused by pathogenic fungi. In one embodiment, the composition of the disclosure comprises a wax selected from the group consisting of polyethylene wax, camuba wax, paraffin wax, polypropylene wax, oxidized polyethylene wax, montan wax, microcrystalline wax, Fischer-Tropsch wax, amide wax, ethylene-acrylic-acid wax, polyolefin wax, ethylene bis stearamide wax, bees wax, lanolin wax, candelilla wax, carnauba wax, esparto grass wax, cork wax, guaruma wax, rice germ oil wax, sugarcane wax, berry wax, ouricury wax, jojoba wax, shea butter, shellac wax, spermaceti, uropygial grease, ceresin, ozocerite (earth wax), sunflower wax, lemon wax, grape fruit wax, laurel wax and vegetable wax and softening agent in a 10:1 to 1:10 ratio (typically about 1:5 ratio), zinc sulfate and boric acid. The softening agent is typically an oil. Exemplary oils include, but are not limited to, mineral oil, corn oil, casteroil, palm oil, palm kernel oil, soybean oil, cottonseed oil, tall oil, lard oil, oleic oil, rape oil, linseed oil, olive oil, peanut oil, fish oil, soybean oil, sesame oil, hemp seed oil, perilla oil, styrax oil, oiticica oil, kayo oil, walnut oil, cashew oil, poppy seed oil, safflower oil, watermelon seed oil, sunflower oil, rice bran oil, pumpkin seed oil, tsubaki oil, crystalis oil, kaoliang oil, ergot oil, bone oil, shark oil, sardine oil, pike oil, herring oil, saurel oil, cod oil, cuttlefish oil, trout oil, mullet oil, tuna oil, menuke oil, menhadden oil, eel oil, whale oil, liver oil, chinawood oil, plant oil, vegetable oil and animal oil. In one embodiment, the oil is mineral oil. The amount of oil (e.g., mineral oil) can be in any ratio with the wax that provides sufficient or a desired malleability to the composition. The amount of oil used will depend upon, for example, the type of wax, the temperature at the site of application and the like. This composition can be applied, for example, to grapevine pruning wounds as a physical barrier against the infection by fungal pathogen while substantially maintaining the natural beneficial flora of the pruning wound.

The compositions of the disclosure can be made, for example, by mixing a wax selected from the group consisting of polyethylene wax, camuba wax, paraffin wax, polypropylene wax, oxidized polyethylene wax, montan wax, microcrystalline wax, Fischer-Tropsch wax, amide wax, ethylene-acrylic-acid wax, polyolefin wax, ethylene bis stearamide wax, bees wax, lanolin wax, candelilla wax, carnauba wax, esparto grass wax, cork wax, guaruma wax, rice germ oil wax, sugarcane wax, berry wax, ouricury wax, jojoba wax, shea butter, shellac wax, spermaceti, uropygial grease, ceresin, ozocerite (earth wax), sunflower wax, lemon wax, grape fruit wax, laurel wax and vegetable wax and mineral oil in a 1:5 ratio to soften the wax (e.g., softening bees wax). The wax, such as bees wax, is melted and mineral oil is added to the wax. After the two components are mixed homogenously, the mixture is left at room temperature to cool. Zinc sulfate and boric acid are then added to the soft wax at the concentration of about 0.1% to about 10%. For example, the amount of zinc sulfate (or other salt thereof) can comprise from about 0.01 to about 9.99% of the composition and the amount of boric acid (or other salt thereof) can comprise from about 0.01 to about 9.99% of the composition. The ratio of zinc sulfate to boric acid can range from 1:100 to 100:1. In one embodiment, the amount of zinc sulfate and boric acid are in equal ratios (e.g., 0.05% to about 5% each of zinc sulfate and boric acid). In one embodiment the zinc sulfate and boric acid are present at 2.5% of the composition. The amount of boric acid and zinc sulfate should be compatible and non-toxic to the plant, vine or tree. Thus, the amount can be varied so long as it does not cause injury to the site of application.

The compositions of the disclosure may further comprise an inert carrier, a preservative, a binder, an emulsifier, a dye, a UV protectant, a buffer, fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular target pathogens.

The composition may further comprise surface-active agents. Suitable surface-active agents include, but are not limited to, anionic compounds such as a carboxylate of, for example, a metal; carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Other inert materials may be included in the compositions. Examples of inert material include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions of the disclosure can be in a suitable form for direct application or as a concentrate of primary composition that requires dilution with a suitable quantity of water or other diluent before application.

A compositions of the disclosure can be applied by painting or spraying a pruning wound.

The disclosure also provides a method of reducing or treating trunk disease comprising contacting a pruning wound or other trunk wound of a plant, vine or tree with a composition of the disclosure. In one embodiment, the composition comprising a wax (e.g., beeswax), zinc and boron is applied immediately after pruning a plant, vine or tree. The composition is applied generously to cover the pruning wound and may be reapplied as needed of the course of several days. In another embodiment, the composition is applied to a trunk wound that may result from injury (e.g., breaking of a branch or vine).

EXAMPLES

The disclosure identifies pruning wound treatments that can be used in organic agriculture. For example, the composition can be used in organic grape production systems. The disclosure can be demonstrated in the effects in six commercial vineyards located in different counties across California, to insure of the efficacy of the compositions (e.g., beeswax compositions) in a range of environmental conditions. Wine grape vineyards located in 6 Counties across California (e.g., Sonoma, Napa, Lodi, Yolo, Santa Barbara, and Riverside Counties) are used.

Vineyards will be pruned in February. Individual grapevines will be randomly assigned one of the following treatments: (1) water control (2) Topsin M (industry standard); (3) Beeswax; (4) BZwax (beeswax with zinc and boron); (5) B-Lock (Table 1). Each treatment will be applied on all pruning of the grapevine. Treatment will be replicated 4 times so that 4 grapevines are treated with one material. Application of products on pruning wounds will be made with a bottle spray (treatment 1 and 2) and spatula (treatment 3, 4, 5). All pruning wounds of a treated grapevine will be artificially inoculated with 10 µl of fungal aqueous spores suspensions (100 spores/µl). Treated grapevine will be inoculated with 4 major fungi causing trunk diseases, namely $T.$ $minima$, $P.$ $chlamydospora$, $E.$ $lata$, and $D.$ $seriata$. A total of 80 grapevines will needed for each experiment (5 treatments×4 replications×5 fungi). Treated wood samples will be collected after harvest, and brought back to the laboratory. Phytotoxicity for each treatment will be rated by recording the percent of bud failure. Fungal recovery from treated wood tissue will be done on Potato Dextrose Agar (PDA) amended with tetracycline. For each treatment, efficacy will be reported as a measure of percent of re-isolation of fungi, which is calculated by the number of infected wood samples over the total number of inoculated wood samples. The data will be analyzed using a weighted least square ANOVA with Dunnett's comparison test to determine if there were significant differences among least square means.

TABLE 1

Product name, active ingredient, percent active ingredient and rate that will be evaluated in field trials.

| Treatment | Product Name | Active Ingredient | Percent Active Ingredient | Rate |
|---|---|---|---|---|
| 1 | Water control | N/A | N/A | N/A |
| 2 | Topsin ® M 70WP | Thiophanate-methyl | 70 | 3.2 oz |
| 3 | Beeswax | N/A | N/A | N/A |
| 4 | BZwax | Boron | 17.5 | 2.5% |
|   |   | Zinc | 22 | 2.5% |
| 5 | B-Lock | Boron | 17.5 | 5% |

N/A: Not Applicable

In an initial trial, an organic sealant comprising 1 part beeswax to 5 parts oil reduced infection rate of pruning wounds from 25 to 60% in field trials.

In another initial trial, an organic sealant comprising 1 part beeswax to 5 parts oil plus 2.5% zinc sulfate and 2.5% boric acid reduced infection rate of pruning wounds from 50 to 90% in field trials.

Other embodiments, combinations and modifications of this invention will occur readily to those of ordinary skill in the art in view of these teachings. Therefore, this invention is to be limited only by the following claims, which include all such embodiments and modifications when viewed in conjunction with the above specification and accompanying drawings.

What is claimed is:

1. A composition for pruning wounds on plants, vines or trees comprising
    a wax selected from the group consisting of polyethylene wax, camuba wax, paraffin wax, polypropylene wax, oxidized polyethylene wax, montan wax, microcrystalline wax, Fischer-Tropsch wax, amide wax, ethylene-acrylic-acid wax, polyolefin wax, ethylene bis stearamide wax, bees wax, lanolin wax, candelilla wax, carnauba wax, esparto grass wax, cork wax, guaruma wax, rice germ oil wax, sugarcane wax, berry wax, ouricury wax, jojoba wax, shea butter, shellac wax, spermaceti, uropygial grease, ceresin, ozocerite, sunflower wax, lemon wax, grapefruit wax, laurel wax and vegetable wax;
    mineral oil; and
    a zinc sulfate and a boric acid, or zinc sulfate and boronic acid or zinc sulfate and boronic ester,
    wherein the zinc sulfate comprises a concentration of 2.5% of the composition and wherein the ratio of wax to mineral oil is 1:5.

2. The composition of claim 1, wherein the wax is bees wax.

3. The composition of claim 1, comprising boric acid.

4. The composition of claim 1, wherein the zinc sulfate and boric acid, or zinc sulfate and boronic acid or zinc sulfate and boronic ester are at equal ratios.

5. The composition of claim 4, wherein the composition comprises 2.5% zinc sulfate and 2.5% boric acid.

6. The composition of claim 1, wherein the composition is formulated to be sprayed or painted on a wound on a plant, vine or tree.

7. The composition of claim 1, wherein the composition comprises a 1:5 ratio of beeswax to mineral oil and the zinc sulfate and boric acid are 2.5% each of the composition.

* * * * *